United States Patent [19]

Bischoff et al.

[11] Patent Number: 4,770,876

[45] Date of Patent: Sep. 13, 1988

[54] MICROBIOLOGICAL PRODUCTION OF LIVESTOCK GROWTH-PROMOTING AGENT

[75] Inventors: Erwin Bischoff, Wuppertal; Hartwig Müller, Velbert; Olga Salcher, Wuppertal; Friedrich Berschauer, Wuppertal; Martin Scheer, Wuppertal; Anno de Jong, Wuppertal; Klaus Frobel, Wuppertal, all of Fed. Rep. of Germany

[73] Assignee: Bayer Aktiengesellschaft, Leverkusen, Fed. Rep. of Germany

[21] Appl. No.: 89,390

[22] Filed: Aug. 25, 1987

[30] Foreign Application Priority Data

Sep. 12, 1986 [DE] Fed. Rep. of Germany ....... 3631008

[51] Int. Cl.$^4$ .......................... A61K 35/74; C12P 1/06
[52] U.S. Cl. ...................................... 424/119; 435/169
[58] Field of Search ......................... 424/119; 435/169

[56] References Cited

PUBLICATIONS

R. B. Woodward, Angew. Chem. 69 50–51 (1957).
Williams, S. T. and Cross, T. (1971), Actinomycetes, pp. 295–334 Booth.

*Primary Examiner*—Jerome D. Goldberg
*Attorney, Agent, or Firm*—Sprung Horn Kramer & Woods

[57] ABSTRACT

Promoting the growth of animals with a novel compound, named annomycin, by cultivation of Streptomyces strain BS 572, DSM 3817.

4 Claims, 2 Drawing Sheets

⊗ Solvens

MICROBIOLOGICAL PRODUCTION OF LIVESTOCK GROWTH-PROMOTING AGENT

The present invention relates to a new organochemical compound, microbiological processes for its preparation, and its use as an agent for increasing production in livestock.

The compound according to the invention can be characterized by the following properties and parameters:

1. IR KBr absorption spectrum

This shows characteristic absorption bands at the following wavelengths (expressed in $cm^{-1}$)

3388
2936
1731
1639
1536
1409
1355
1188
1073
972
811
652

Figure 1:
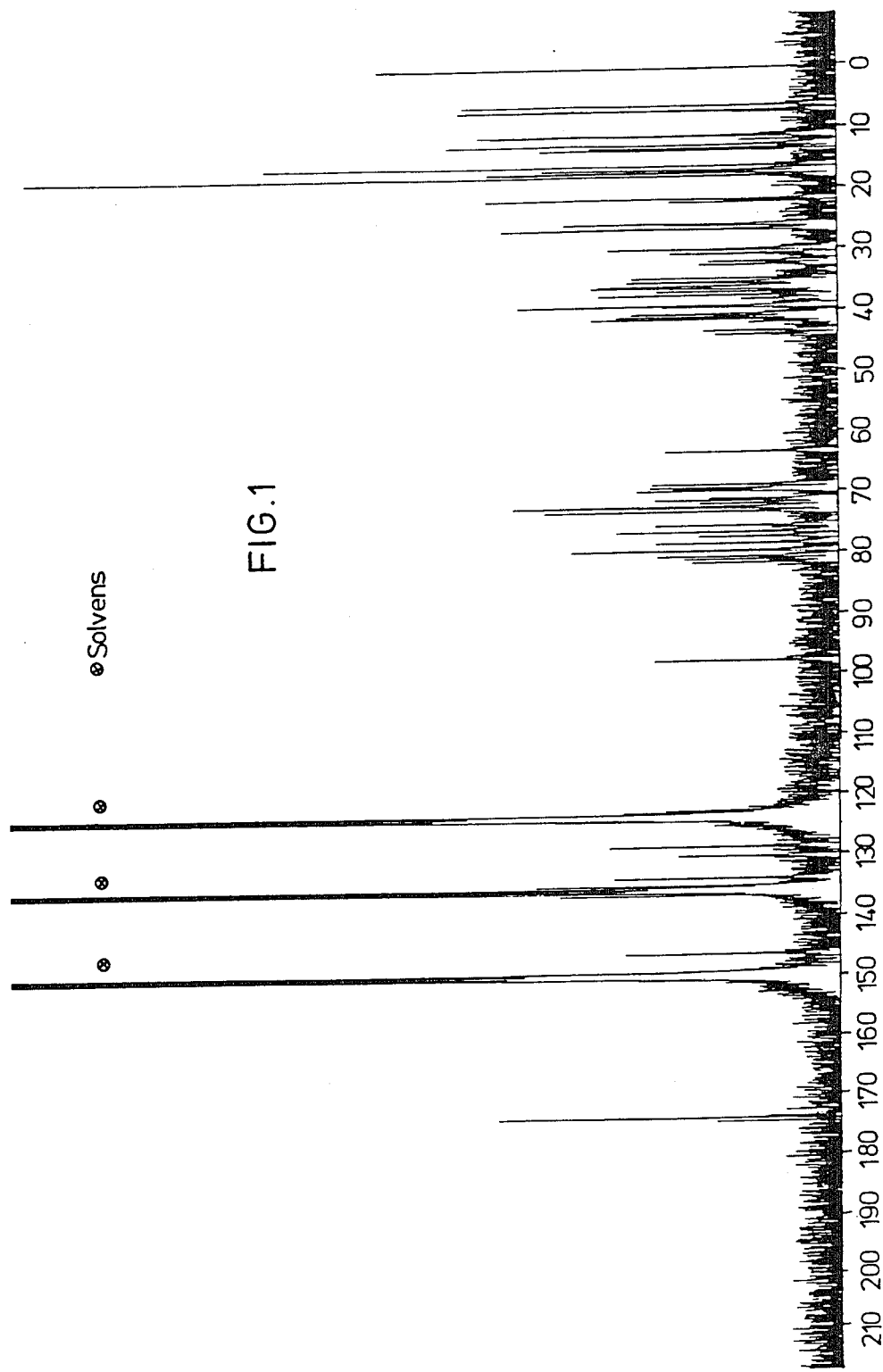

2. 13C nuclear magnetic resonance spectrum of the antibiotic in pyridine, as shown in FIG. 1, specified in parts per million.

The spectrum was recorded at a field strength of 75.48 MHz on a solution of the antibiotic in deuterated pyridine with tetramethylsilane as internal standard.

Figure 2:
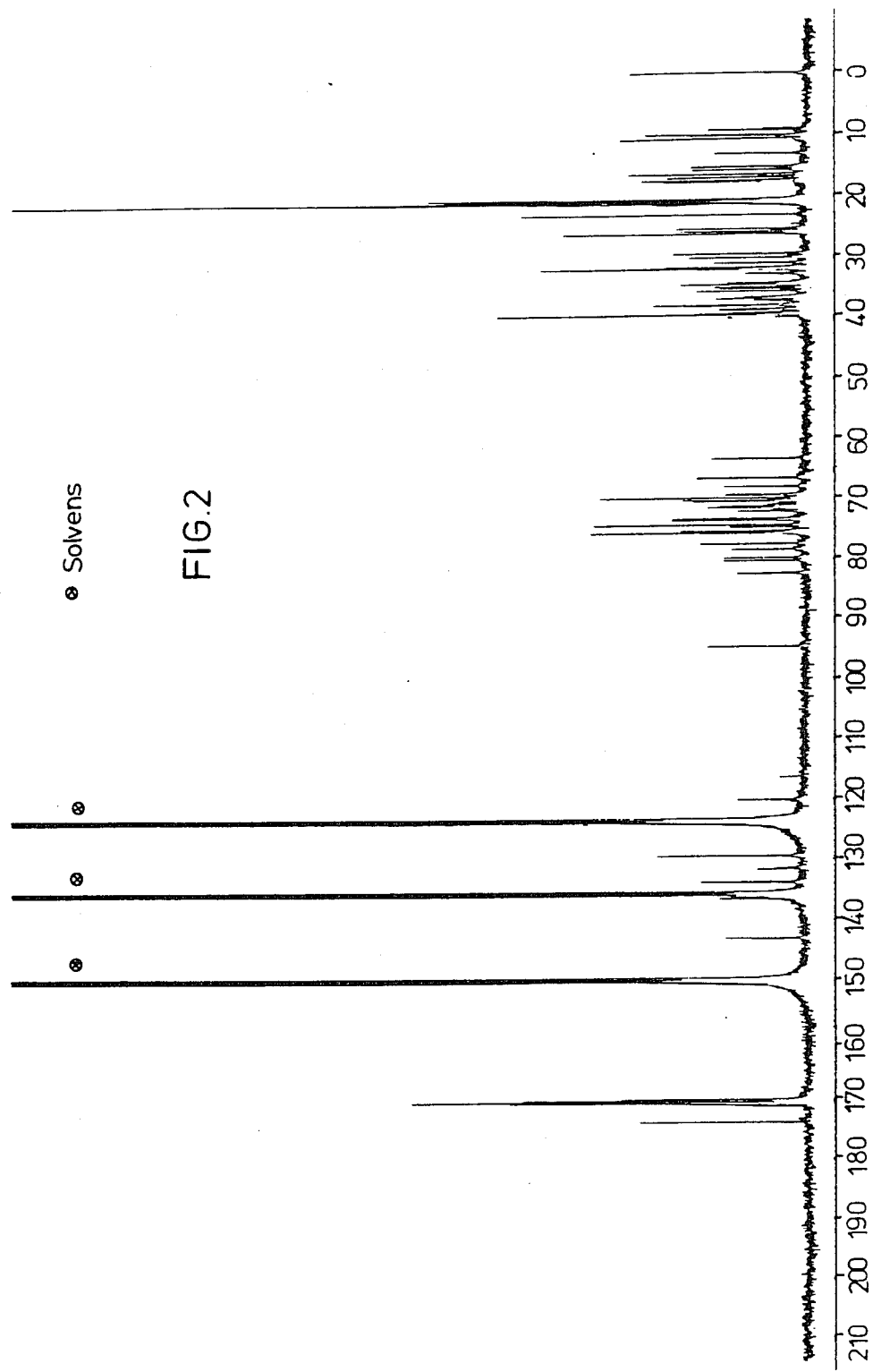

3. The 13C nuclear magnetic resonance spectrum of the antibiotic, as shown in FIG. 2, after reaction with acetic anhydride, recorded in deuterated pyridine, specified in parts per million.

The spectrum was recorded at a field strength of 75.48 MHz on a solution of the acetate in deuterated pyridine with tetramethylsilane as internal standard.

4. Elemental analysis (after drying for 2 days in a high vacuum at 30° C.):

C 57.4–56.8
H 8.6–8.8
N 3.3–3.4
O 26.1–28.3

It must be pointed out here that, in the case of high molecular weight natural products, the range of error for elemental analysis can be greater than is generally usual; for this reason, exact determination of the empirical formula is not possible (R. B. Woodward, Angew. Chem. 69, 50–51 (1957)).

5. After chromatography on silica gel thin-layer plates, the compound can be stained with thymol/H$_2$SO$_4$ or Cl$_2$/tolidine reagent. The reagents were prepared by general procedures (cf. E. Stahl, Dünnschichtchromatographie [Thin-layer chromatography], 2nd edition, Springer Verlag, Berlin, Heidelberg, New York 1967).

6. The antibacterial action of the compound is shown in Table 1.

The new antibiotic according to the invention is given the name annomycin.

The present invention furthermore relates to new microorganisms of the Streptomycetaceae family which, on cultivation in a nutrient medium containing carbon and nitrogen sources and mineral salts, produce a compound which has the properties and parameters shown under (1) to (5).

Of these, the new microorganism strain BS 572 of the genus Streptomyces is particularly important in the context of the present invention.

The strain was concentrated and isolated, according to conventional actinomycetes isolation methods, by plating out soil sample suspensions in Petri dishes, incubating them for four to six weeks and repeatedly subculturing individual colonies (Williams, S. T. and Cross, T. (1971). Actinomycetes. In Methods in Microbiology, 4 295–334. Booth, C. (editor), London-New York: Academic Press).

The new Streptomyces strain with the laboratory designation BS 572 was filed under the number DSM 3817 with the German Register of Microorganisms, Grisebachstrasse 8, 3400 Göttingen, FRG, on Aug. 13, 1986.

It has furthermore been found that the compound according to the invention is obtained when suitable microorganisms of the Streptomycetaceae family are cultivated under aerobic conditions in a nutrient medium which contains assimilatable carbon and nitrogen sources and mineral salts, and the compound is isolated by conventional methods.

In order to carry out the process according to the invention, the Streptomycetes strain BS 572 (and its mutants and variants), in particular, can be used.

This strain belongs to the bacteria of the actinomycetales order, the Streptomycetaceae family and the Streptomyces genus. It was isolated from soil.

The BS 572 strain was determined taxonomically according to Bergey's Manual of Determinative Bacteriology 8th edition (974) and International Journal of Systematic Bacteriology 16, 313–340 (1966) and The Prokaryotes 2, 2028–2090 (1981).

1. Morphology

Moderate sporulation could only be observed on basal agar with raffinose and galactose (ISP medium No. 9) and on ISP medium No. 3+7. On other media (ISP media Nos. 1+2 and 4–6), very little aerial mycelium or only substrate mycelium was formed.

Aerial mycelium (ISP medium No. 9; 28° C.; 7 days):
Color: pale pink after 7 days
Spore chain: RF type or spore Chain morphology: Rectus flexibilis
Spores: smooth (electron microscopy), cylindrical about 1.2–1.4 µm broad, 1.8–2.4 µm long.
Substrate mycelium:
Color: pale brown to red-brown 2. Physiology The optimum temperature is 28° (ISP medium No. 2, 2 days). The growth was inhibited by chloramphenicol (10 µg); erythromycin (10 µg), sulphafurazole (100 µg), streptomycin (10 µg), tetracycline (10 µg), fusidic acid (10 µg) and novobiocin (5 µg) (ISP medium No. 2, 28° C., 2 days). Good growth (substrate mycelium) occurs on ISP media Nos. 3+7 with sparse aerial mycelium formation in ISP medium No. 3.

The composition of the media, described above, in which sporulation of BS 572 occurred is described below:

| ISP medium No. 7 (tyrosine agar) | |
|---|---|
| glycerol | 15 g |
| L-tyrosine | 0.5 g |
| L-asparagine | 1 g |
| K$_2$HPO$_4$ (anhydrous) | 0.5 g |
| MgSO$_4$.7H$_2$O | 0.5 g |
| NaCl | 0.5 g |

| -continued | |
|---|---|
| FeSO$_4$.7H$_2$O | 0.01 g |
| H$_2$O, deionized | 1000 ml |
| Trace-element solution | 1 ml |
| pH 7.2–7.4 | |
| Bacto-Agar | 20 g |
| Trace-element solution | |
| FeSO$_4$.7H$_2$O | 0.1 g |
| MnCl$_2$.4H$_2$O | 0.1 g |
| ZnSO$_4$.7H$_2$O | 0.1 g |
| H$_2$O, deionized | 100 ml |
| Basal agar with raffinose or galactose | |
| (NH$_4$)$_2$SO$_4$ | 2.64 g |
| KH$_2$PO$_4$ (anhydrous) | 2.38 g |
| K$_2$HPO$_4$.3H$_2$O | 5.65 g |
| MgSO$_4$.7H$_2$O | 1.00 g |
| Pridham and Gottlieb trace-element solution (B) | 1.00 ml |
| H$_2$O, deionized | 1000 ml |
| pH 6.8–7.0 | |
| Difco Agar | 15 g |
| Raffinose or galactose | 10 g* |
| Pridham and Gottlieb trace-element solution (B) | |
| CuSO$_4$.5H$_2$O | 0.64 g |
| FeSO$_4$.7H$_2$O | 0.11 g |
| MnCl$_2$.4H$_2$O | 0.79 g |
| ZnSO$_4$.7H$_2$O | 0.15 g |
| H$_2$O, deionized | 100 ml |

For further media, see Int. J. Syst. Bact 16, 313–340 (1966).
*After autoclaving, solutions of raffinose or galactose, filtered under sterile conditions, are added. Final concentration 10 g per liter.

The utilization of C sources was checked on basal agar according to Int. I. Syst. Bact. 16, 313–240 (1966). For the negative control, the growth on basal agar without a C source was compared.

| C source (10 g/l) | Growth* |
|---|---|
| control (no C source) | − |
| D-glucose | ± |
| D-xylose | ± |
| D-arabinose | − |
| L-rhamnose | + |
| D-fructose | − |
| D-galactose | + |
| raffinose | + |
| D-mannitol | + |
| meso-inositol | − |
| salicin | − |
| saccharose | − |
| ribose | + |
| mannose | + |
| maltose | − |
| lactose | − |
| melibiose | − |
| cellulose | − |
| acetate | − |

*+ = growth;
− = no growth;
± = result ambiguous

Due to the morphological data, strain BS 572, isolated from a soil sample from Israel (Jerusalem), can be allocated to the Cinnamomeus group of Streptomycetes. The physiological properties do not fully agree with any of the strains described in Bergey's Manual.

Taxonomic designation: Streptomyces sp.

For the process for the preparation of the compound according to the invention, nutrient media which contain conventional carbon and nitrogen sources and the necessary salts are used. The following can be used as a carbon source:

Carbohydrates, in particular polysaccharides, such as, for example, starch, oligosaccharides, such as, for example, raffinose, and monosaccharides, such as, for example, mannose and galactose. Furthermore, sugar alcohols, such as, for example, mannitol and glycerol, are also suitable as a carbohydrate source. In addition, naturally occurring mixtures, such as, for example, malt extract or distiller soluble, and mixtures of the possibilities mentioned, can also be used.

As N source, the conventional nitrogen-containing nutrient media components can be used, such as, for example, amino acids, proteins, hydrolyzed protein, ammonium salts, naturally occurring complex substances, such as soybean meal, milk powder and suitable mixtures thereof.

Mineral salts are required in the nutrient medium as auxiliaries, for example phosphates, sulphates or chlorides, of potassium, of sodium, of calcium, of magnesium, iron, zinc and manganese. The concentration of these substances can vary within broad limits, and the concentrations of mineral salts necessary are sometimes present in the carbon or nitrogen sources mentioned or in the water used as impurities.

Furthermore, antifoam agents of a very wide variety of types, such as, for example, polyols or silicones, can also be used as auxiliaries.

The process for the preparation of the compound according to the invention can be carried out with the aid of conventional solid, semi-solid or liquid nutrient media. Aqueous liquid nutrient media are preferred.

In this process, the nutrient media are inoculated by generally conventional methods, for example via inclined tubes or flask cultures.

The culture is carried out under aerobic conditions and can be carried out according to generally conventional methods, such as using shake cultures, for example in shaking flasks, air-agitated cultures or submerged cultures. The cultivation is preferably carried out using the aerobic submersion process in aerated fermenters, for example in conventional submersion fermentation tanks. It is possible to carry out the culture continuously or batchwise. A batchwise procedure is preferred.

When carrying out the preparation process, aerobic conditions are used; the culture can be carried out according to conventional methods, such as, for example using shake cultures or aerated fermenter cultures. The percentage ratios of the nutrient solution components can vary within broad ranges, but in general, the carbon sources make up 0.5 to 8%, preferably 0.6 to 6%, the nitrogen sources 0.1 to 5%, preferably 0.5 to 2%, and the salts are present in conventional concentrations, preferably in the range between 0.001 to 0.5% by weight. The antifoam agents are present in a concentration of up to 0.5%. The sterilization temperatures used are 100° to 140° C., preferably 120° to 130° C.

The pH of the growing cultures should preferably be kept between about 6 and 8.5, in particular between 6.5 and 8.0. An excessively steep pH decrease into the acidic region can be prevented by adding an organic or inorganic base, preferably CaCO$_3$. As is conventional in fermentation technology, automatic pH regulation, in which sterile organic or inorganic acids, for example H$_2$SO$_4$, or sterile lyes, for example NaOH, are injected at intervals into the culture solution, can also be used.

It is expedient to ensure that the microorganisms are brought into contact with oxygen and the nutrients to an adequate extent. This can be done by conventional methods, such as shaking and stirring.

The cultivation temperature can be between about 16° and about 42° C., preferably between 24° and 32° C., particularly preferably about 28° C. The cultivation duration can be varied widely, the composition of the nutrient medium and the cultivation temperature, for example, playing a part in this duration. The ideal conditions in each case can easily be determined by those skilled in microbiology.

It has become apparent that the amount of the compound, according to the invention, concentrating in the culture broth generally reaches its maximum about 1 to 7, preferably 1 to 4, days after commencement of cultivation.

As is general in microbiological processes, foreign infections should be prevented in the culture media. To this purpose, the conventional precautions should be taken, such as sterilization of the nutrient media, the culture flasks and the air necessary for aeration. For sterilization of the equipment, steam or dry sterilization, for example, can be used.

If foam is produced in an undesired quantity during cultivation, conventional chemical antifoam agents, for example liquid fats and oils, oil/water emulsions, paraffins, higher alcohols, such as octadecanol, silicone oils, and polyoxyethylene and polyoxypropylene compounds, can be added. Foam can also be suppressed or eliminated with the aid of conventional mechanical devices (which use, for example, centrifugal forces).

The active compound according to the invention exhibits an antibiotic activity against Gram-positive bacteria.

The microbiological activity of annomycin is described in Table 1. The test method was the conventional agar diffusion method. 100 μl of a methanolic solution of the active compound according to the invention, annomycin, in the concentrations specified are transferred into the prepunched holes (φ 9 mm) of a nutrient medium containing the specified titre of the test germ. The agar plates are subsequently incubated at the temperature specified. After the incubation time specified, the diameter of the area of inhibition caused by annomycin is measured.

tional physical/chemical methods. The isolation can be effected, for example, according to conventional extraction processes, precipitation processes and/or chromatography processes. The isolated compound can also be ultrapurified with the aid of the methods mentioned. However, in many cases ultrapurification is not necessary since the impurities which may be present do not affect the activity of the compound in a disadvantageous manner.

In the abovementioned isolation and purification methods, in order to discover which fractions contain the compound according to the invention in the highest concentration and purity, determination of the antibiotic activity is preferably employed. Suitable test germs in this determination are particularly *Staphylococcus aureus* 1756 and *Bac. subtilis* ATCC 27859.

The compound according to the invention can be isolated and purified, for example in the case where a liquid aqueous nutrient medium is used, as follows: after concentration in the culture supernatant, the culture fitrate and mycelium are separated using conventional methods (for example centrifugation).

The compound according to the invention can be isolated from the culture filtrate with the aid of conventional extraction processes, precipitation processes and/or chromatography processes, and, if appropirate, can be purified. The chromatography can be carried out in the form of column chromatography. Adsorbents which can be employed are conventional inorganic or organic adsorbents, such as, for example, aluminum oxide, silica gel, magnesium silicate, activated charcoal, cellulose, cellulose derivatives, synthetic resins, such as polyamides, for example acetylated polyamide, or dextran gels. As eluants, a very wide variety of solvents or solvent mixtures in which the compound according to the invention is soluble can be used. Preferably employed is methanol or a mixture of butanol: glacial acetic acid: $H_2O$ in the ratio 2:1:1.

TABLE 1

| | Range of action of annomycin | | | | | |
|---|---|---|---|---|---|---|
| | Diameter of inhibited area in mm at concentration | | Nutrient | | | Incubation |
| Test germ: | 0.2 mg/ml | 1 mg/ml | medium | Titre | Temperature | time |
| *Arthrobacter oxidans* DSM 20119 | 15 | 19 | St 1 | $1 \times 10^5$ | 28° C. | 40 h |
| *Arthrobacter simplex* NCIB 9770 | 15 | 20 | St 1 | $1 \times 10^6$ | 28° C. | 48 h |
| *Bacillus brevis* (Spores) DSM 298 | 10 | 14 | A 3 | $1 \times 10^6$ | 37° C. | 16 h |
| *Bacillus cercus* (Spores) DSM 318 | 11 | 16 (24) | A 3 | $1 \times 10^6$ | 37° C. | 16 h |
| *Bacillus subtilis* (Spores) ATCC 6633 | 12 | 18 | A 3 | $1 \times 10^6$ | 37° C. | 16 h |
| *Bacillus subtilis* (Spores) ATCC 27859 | 25 | 31 | A 3 | $1 \times 10^6$ | 37° C. | 16 h |
| *Cornynebacterium facians* DSM 20131 | 14 (23) | 20 (30) | St 1 | $1 \times 10^6$ | 28° C. | 40 h |
| *E. coli* 14 | — | — | A 3 | $1 \times 10^6$ | 37° C. | 16 h |
| *E. coli* A 261 | — | — | A 3 | $1 \times 10^6$ | 37° C. | 16 h |
| *E. coli* ATCC 9637 | — | — | A 3 | $1 \times 10^6$ | 37° C. | 16 h |
| *E. coli* ATCC 11105 | — | — | A 3 | $1 \times 10^6$ | 37° C. | 16 h |
| *E. coli* ATCC 25290 | — | — | A 3 | $1 \times 10^6$ | 37° C. | 16 h |
| *Klebsiella pneumoniae* DSM 30102 | — | — | A 3 | $1 \times 10^6$ | 37° C. | 16 h |
| *Micrococcus luteus* | 23 | 28 | A 3 | $1 \times 10^6$ | 37° C. | 16 h |
| *Proteus vulgaris* | — | — | A 3 | $1 \times 10^6$ | 37° C. | 16 h |
| *Pseudomonas aeruginosa* | — | — | A 3 | $1 \times 10^6$ | 37° C. | 16 h |
| *Serratia marcescens* | — | — | A 3 | $1 \times 10^6$ | 37° C. | 16 h |
| *Staphylococcus aureus* 1756 | 12 | 20 | A 3 | $1 \times 10^6$ | 37° C. | 16 h |
| *Staphylococcus aureus* P 209 | 13 | 21 | A 3 | $1 \times 10^6$ | 37° C. | 16 h |
| *Saccharomyces cerevisiae* | — | — | YM | $1 \times 10^4$ | 28° C. | 16 h |
| *Piricularia orycae* (Spores) DSM 62938 | — | — | YM | $1 \times 10^4$ | 22° C. | 20 h |

Nutrient medium:
St 1 = standard 1 nutrient broth (Merck 7882) + 15 g of Bacto Agar per liter
YM = yeast malt according to ATCC 196 + 15 g of Bacto Agar per liter
A 3 = antibiotic medium 3 (Difco 0243-01-6) + 15 g of Bacto Agar per liter The compound according to the invention can be isolated from the culture medium by generally conven- Chromatography processes, for example non-specific adsorption on hydrophobic sorbents or, on the other hand, gel diffusion chromatography, are preferably used for isolating the compound according to the invention.

The commercial preparation of the compound according to the invention is preferably carried out by adsorption and subsequent desorption on a hydrophobic support resin (for example Lewapol ®; a hydrophobic support resin supplied by Bayer AG). Desorption can be carried out, for example, using short-chain aliphatic alcohols, preferably methanol or ethanol.

A fraction prepurified in this fashion can be repurified using conventional methods. Gel diffusion chromatography can advantageously be employed here. Chromatography on Sephadex LH-20 ® proceeds successfully. A product obtained in this fashion is generally purer than 40%.

The compound according to the invention can be isolated from the mycelium. To this purpose, the mycelium is separated from the culture broth, preferably by centrifugation, and extracted repeatedly, preferably twice, with a water-miscible solvent. Solvents which can be used here are lower alkylalcohols ($C_1$-$C_4$), such as ethanol or isopropanol, and ketones, acetone being particularly preferred. The aqueous organic solution is concentrated in vacuo until the organic phase has distilled off. The residue is now diluted with water to the corresponding volume of the culture broth and freeze-dried, and the work-up is continued as specified below.

The compound according to the invention can also be isolated from the culture filtrate by adsorption on activated charcoal or on suitable resins. A particularly suitable method has proved to be bonding the compound according to the invention to non-specific adsorber resins based on polystyrene (for example Amberlite XAD ® supplied by Roehm & Haas or Lewapol OC 1031 ® supplied by Bayer). The desorption of the compound according to the invention is carried out fractionally through mixtures of water and organic solvents, in particular water/methanol. Fractions which were determined as active by the test against *Staphylococcus aureus* 1756 are concentrated under reduced pressure until the organic solvent has been removed completely, and the residue is suspended in about 1/50 of the culture filtrate volume and freeze-dried.

Isolation from the culture filtrate is preferred. The lyophylizate is extracted with water and centrifuged, and the residue is resuspended in water and freeze-dried. The lyophylizate thus obtained is then dissolved in a mixture of methanol/water with addition of acetic acid. The active compound can be obtained from the solution by conventional chromatographic methods, preferably chromatography on Sephadex LH 20 ® or by "reversed phase" liquid high-pressure chromatography.

The active compound is employed as a production improver in livestock for promoting and accelerating growth and milk and wool production, and for improving feed utilization and meat quality, and for shifting the meat/fat ratio in favor of the meat. The suitability of annomycin for preventing and curing dysentery in pigs and ketosis in dairy cattle should be mentioned in particular. The active compound is preferably used for livestock animals. Livestock animals include ruminants, such as, for example, cattle, sheep and goats.

Irrespective of the sex of the animals, the active compound is employed in all growth and production phases of the livestock. The active compound is preferably employed in the intensive growth and production phase. Depending on the type of animals, the intensive growth and production phase lasts from one month to 10 years.

The amount of active compound which is administered to the animals in order to achieve the desired effect may be varied substantially as a result of the favorable properties of the active compound. This amount is preferably about 0.001 to 50 mg/kg, particularly 0.01 to 5 mg/kg of body weight per day. The suitable amount of the active compound and the suitable duration of the administration depend, in particular, on the species, the age, the sex, the growth and production phase, the health and the type of keeping and feeding of the livestock, and can easily be determined by any expert.

The active compound is administered to the livestock by conventional methods. The type of administration depends, in particular, on the species, the behavior and the health of the livestock.

The active compound may be administered once. However, the active compound may also be administered temporarily or continuously over the entire growth and production phase or over part of the growth and production phase. In the case of continuous administration, administration can be carried out once or several times daily at regular or irregular intervals.

Administration is effected orally in formulations which are suitable for this or in pure form.

The active compound may be present in the formulations alone or mixed with other production-promoting active compounds such as antibiotics, mineral feedstuffs, trace element compounds, vitamins, non-protein compounds, colorants, antioxidants, aromas, emulsifiers, flow auxiliaries, preservatives and tabletting auxiliaries.

Antibiotics are, for example, tylosin and virginiamycin. Mineral feedstuffs are, for example, dicalcium phosphate, magnesium oxide and sodium chloride. Trace element compounds are, for example, iron fumarate, sodium iodide, cobalt chloride, copper sulphate and zinc oxide. Vitamins are, for example, vitamin A, vitamin $D_3$ and vitamin E. Non-protein compounds are for example. biuret and urea. Colorants are, for example, carotinoids, such as citranaxanthin, zeaxanthin and capsanthin. Antioxidants are, for example, ethoxyquin and butylhydroxytoluene. Aromas are, for example, vanillin. Emulsifiers are, for example, esters of lactic acid, and lecithin. Flow auxiliaries are, for example, sodium stearate and calcium stearate. Preservatives are, for example, citric acid and propionic acid. Tabletting auxiliaries are, for example, ligninsulphonates and cellulose ethers.

The active compound may also be administered together with the feed and/or with the drinking water.

The feed includes individual feedstuffs of vegetable origin, such as hay, beet and cereal by-products, individual feedstuffs of animal origin, such as meat, fats, milk products, bonemeal and fish products, individual feedstuffs such as vitamins, proteins, amino acids, for example DL-methionin, and salts such as lime and common salt. The feed also includes supplementary feed, prepared feed and compound feed. These contain individual feedstuffs in a composition which ensures balanced nutrition with respect to the energy and protein supply and with respect to the supply of vitamins, mineral salts and trace elements.

The concentration of the active compound in the feed is normally about 1–500 ppm, preferably 30–200 ppm.

The active compound may be added to the feed as such or in the form of premixes or feed concentrates.

The following is an example of the composition of a cattle feed which contains the active compound according to the invention:

69.95% feed-grain meal, 10% of ground corn cobs, 8% of soybean meal, 5% of alfalfa meal, 5% of molasses, 0.6% of urea, 0.5% of calcium phosphate, 0.5% of calcium carbonate, 0.3% of common salt and 0.15% of premix. The premix contains 70,000 I.U. of vitamin A, 7 000 I.U. of vitamin D3, 100 mg of vitamin E, 50 mg of manganese, 30 mg of zinc and 0.06 mg of cobalt.

The active compound is admixed in the amounts necessary with the premix.

It is not absolutely essential to use purified and isolated annomycin. It is also possible to employ the mixture produced during its preparation or even the culture broth produced or mycelium without purification, if appropriate after drying. For many purposes, it is also sufficient to employ crude forms of the compound according to the invention and its mixtures without previous ultrapurification.

The preparation and biological action of the new compound according to the invention can be illustrated by the following examples:

EXAMPLE A

Rumen fluid was removed by means of a rumen fistula from a sheep which had been fed with 650 g of coarsely ground prepared sheep feed and 250 g of dried fodder cobs per day. The prepared feed had been administered via an automatic feeder in 12 equal portions at two-hourly intervals, and the cobs in 2 equal portions at 8.30 and 16.15 hours. The rumen fluid was subjected to the following treatment immediately after removal: 2.5 ml of rumen inoculum were placed in a test tube of volume 13 ml which had been gassed with carbon dioxide and which, in addition, contained the following additives:

100 mg of finely ground prepared sheep feed
7.5 ml of buffer solution
0.5 ml of a 5% strength aqueous ethanol solution with or without the compound according to the invention.

The composition of the buffer solution, which was saturated with carbon dioxide before commencement of the experiment, was as follows:

| Na2HPO4 | 4.61 g per liter of water |
| NaHCO3 | 12.25 g per liter of water |
| NaCl | 0.59 g per liter of water |
| KCl | 0.71 g per liter of water |
| MgCl2 | 0.32 g per liter of water |
| CaCl2 | 0.13 g per liter of water |

Each test tube was sealed with a Bunsen stopper and incubated at 39° C. After 1, 2, 4, 6 and 8 hours, the preparations were shaken manually. After incubating for 24 hours, 1.0 ml of the fermentation liquid was removed from the preparations and pipetted into a Eppendorf vessel containing 0.2 ml of 10% strength phosphoric acid (containing 5.7 μmol of 2-methylvaleric acid). The samples were centrifuged at 11,000 g and the volatile fatty acid concentrations in the supernatant were determined by gas chromatography.

The acetic acid to propionic acid ratio was determined in each experiment. The value obtained in the negative controls was set at 100 and the differences compared to this specified. The more propionic acid which forms, the lower the acetic acid to propionic acid ratio and the smaller the ratio number compared to the control (low ratio number = reduced acetic acid/propionic acid ratio = improved feed utilization).

In addition, the concentrations of total fatty acids compared to the control (=100) are specified in each experiment.

TABLE

| Amount (μg/preparation) | Acetic acid/propionic acid ratio | Total fatty acids |
|---|---|---|
| Control | 100 | 100 |
| 20 | 88.2 | 104.7 |
| 100 | 60.9 | 103.8 |
| 250 | 55.5 | 105.2 |
| 1000 | 41.8 | 103.1 |

EXAMPLE 1

Preparation of the inoculation material for the preculture 150 ml of sterile "nutrient solution A" CASO ® supplied by Merck, Darmstadt, with the composition

| peptone from casein | 15 g |
| peptone from soy meal | 5 g |
| D-glucose | 2.5 g |
| NaCl | 5 g |
| water | to 1000 ml | in a 1 liter conical flask are inoculated with vegetative cells of Streptomycetes strain BS 572 and incubated at 28° C. for 3 days on an orbital shaker at 280 rpm. The cultures grown serve as inoculation material for further fermentation batches.

EXAMPLE 2

Preparation of the preculture 20 liters of nutrient solution of the composition described above and 20 ml of antifoam agent (SAG 5693, Union Carbide) are transferred into a fermenter (30 liters) equipped with stirrer and aeration device, and are sterilized at 120° C. After cooling the solution, the fermenter is inoculated with 300 ml of the shake cultures, obtained as described above, of Streptomycetes strain BS 572, aerated with 10 liters of sterile air per minute (0.5 VVm) at 300 revolutions of the stirrer (blade stirrer) per minute, and fermented at a temperature of 28° C. and a supernatant pressure of 0.5 bar. After fermenting for 2 days, the contents are used as inoculum for a batch in a 600 liter fermenter.

EXAMPLE 3

Tank fermentation 400 liters of nutrient solution of the following composition

| skimmed-milk powder | 10 g |
| yeast autolyzate | 1.5 g |
| dextrin | 40 g |
| D-glucose | 5 g |

-continued

| antifoam agent (SAG 5693 Union Carbide) | 1 ml |
|---|---|
| tap water to | 1000 ml | are adjusted to pH 7 in a 600 liter fermenter, sterilized at 121° C. for 60 minutes, cooled to 28° C. and inoculated with 20 liters of the inoculum obtained according to Example 2. Fermentation was effected at 28° C., an aeration rate of 180 liters of sterile air per minute (0.45 VVm), a supernatant pressure of 1.0 bar and 100 revolutions (blade stirrer) per minute. When annomycin has been formed after fermenting for 3 to 4 days, the culture is gathered.

EXAMPLE 4

(a) The culture broth obtained from a 400 liter fermentation according to Example 3 is separated at about 200 liters/hour in a Westfalia separator. The pH of the supernatant is adjusted to 4.0 using 6N HCl and transferred onto a 30 cm diameter column charged with 50 liters of Lewapol OC 1031 ® (Bayer). Washing is effected successively with 300 liters of demineralized water and 300 liters of (30% strength) aqueous methanol, and desorbing is effected with pure methanol. The desorbate is concentrated under reduced pressure, suspended in about 20 liters of water and lyophilized, 215 g of the crude active compound according to the invention being obtained. The active compound content is 3%.

(b) The mycelium is stirred for 30 minutes with 30 liters of acetone and then filtered. The filter cake is again stirred for 30 minutes with 20 liters of acetone and refiltered. The purified filtrates are now concentrated to about 15 liters under reduced pressure and then diluted to 130 liters with demineralized water. After adjusting the pH to 4.0 using 6N HCl, this solution is transferred onto a 20 cm diameter column charged with 20 liters of Lewapol OC 1031 ®. The column is washed successively with 150 liters of demineralized water and 150 liters of 30% strength aqueous methanol, and desorbed with 150 liters of methanol. The desorbate is now concentrated under reduced pressure, suspended in about 10 liters of water and freeze-dried, 96 g of the crude compound according to the invention being obtained. The active compound content is 3%.

EXAMPLE 5

Purification of the compound according to the invention by extraction, gel chromatography and reversed-phase chromatography 10 g of the crude product obtained according to Example 4a are suspended in 100 ml of water, and the pH is adjusted to 8.0 using 0.2N KOH. The suspension is now stirred for 20 minutes and then centrifuged. The sediment is suspended in 50 ml of water and freeze-dried. 1.5 g of a 12% purity crude product are obtained.

2.7 g of such a crude product are dissolved in 30 ml of a 50% strength aqueous methanolic solution which is 50 mM with respect to acetic acid, and subjected to gel filtration on Sephadex LH 20 ®. A column of diameter 5 cm and length 1 m is used.

The flow rate is 160 ml/hour. 20 ml fractions are taken. The fractions which, according to antibiography, are active against *Staphylococcus aureus* 1756 are combined, concentrated under reduced pressure and freeze-dried. 314 mg of the antibiotic according to the invention having an active compound content of 45% are obtained.

180 mg of the preparation thus obtained are separated in portions of 60 mg via a preparative RP-18 column. A column of diameter 16 mm and length 25 cm, filled with Lichrosorb ® RP 18 7 μm (Merck) is used. The eluent used is a mixture of 0.1M $KH_2PO_4$, adjusted to pH 2.1 using $H_3PO_4$, and acetonitrile in the buffer solution/acetonitrile ratio 6/4. The flow rate is 15 ml/minute. 16-ml fractions are collected. The fractions are analyzed by thin-layer chromatography and the unary and biologically active fractions which can be stained by thymol/$H_2SO_4$ are combined (180 ml) and concentrated to about 70 ml under reduced pressure.

They are transferred to a column of diameter 3 cm and length 100 cm, filled with Sephadex LH 20 ® in 1 mM aqueous acetic acid. The flow rate is 70 ml/hour. 10-ml fraction are taken. The fractions are analyzed as described above, combined and freeze-dried. Yield: 68 mg of a 95% purity product.

It will be understood that the specification and examples are illustrative but not limitative of the present invention and that other embodiments within the spirit and scope of the invention will suggest themselves to those skilled in the art.

We claim:

1. Annomycin which is characterized by the following chemical and physical parameters:

(a) IR KBr absorption spectrum exhibits characteristic absorption bands at the following wavelengths ($cm^{-1}$):
3388
2936
1731
1639
1536
1409
1355
1188
1073
972
811
652

(b) 13C nuclear magnetic resonance spectrum of the antibiotic in deuterated pyridine, as shown in FIG. 1, specified in parts per million, (c) the 13C nuclear magnetic resonance spectrum of the antibiotic, as shown in FIG. 2, after reaction with acetic anydride, recorded in deuterated pyridine, specified in parts per million, (d) elemental analysis (after drying for 2 days in a high vacuum at 30° C.)
C 57.4–56.8
H 8.6–8.8
N 3.3–3.4
O 26.1–28.3

(e) after chromatography on silica gel thin-layer plates, the compound can be stained with thymol/$H_2SO_4$ or $Cl_2$/tolidine reagent, (f) an antibacterial action as shown in Table 1.

2. A process for the preparation of a compound according to claim 1, comprising cultivating Streptomyces strain BS 572, DMS No. 3817, under aerobic conditions in a nutrient medium containing assimilatable carbon and nitrogen sources and mineral salts until a sufficient amount of the compound has been imparted to the medium.

3. A premix or feed additive comprising an amount of the compound according to claim 1 effective for promoting the growth of livestock, and a diluent.

4. A method of promoting the growth of animals which comprises orally administering to said animals a growth-promoting effective amount of a compound according to claim 1.

* * * * *